(12) United States Patent
Champagne (10) Patent No.: US 7,608,217 B2
(45) Date of Patent: Oct. 27, 2009

(54) APPARATUS AND METHOD FOR HUMIDIFYING A STERILIZATION CHAMBER

(75) Inventor: Réal Champagne, Beauport (CA)

(73) Assignee: TSO3, Inc., Sainte-Foy (CA)

( * ) Notice: Subject to any disclaimer, the term of this patent is extended or adjusted under 35 U.S.C. 154(b) by 652 days.

(21) Appl. No.: 10/553,740

(22) PCT Filed: Sep. 7, 2004

(86) PCT No.: PCT/CA2004/004636

§ 371 (c)(1),
(2), (4) Date: Oct. 20, 2005

(87) PCT Pub. No.: WO2005/031220

PCT Pub. Date: Apr. 7, 2005

(65) Prior Publication Data

US 2007/0003429 A1 Jan. 4, 2007

(30) Foreign Application Priority Data

Sep. 26, 2003 (CA) .................................. 2443044

(51) Int. Cl.
*A61L 2/07* (2006.01)

(52) U.S. Cl. .................. 422/3; 422/26; 422/27; 422/33; 422/292

(58) Field of Classification Search ................. None
See application file for complete search history.

(56) References Cited

U.S. PATENT DOCUMENTS

| 4,956,145 | A | 9/1990 | Cummings et al. |
|---|---|---|---|
| 5,344,622 | A | 9/1994 | Faddis et al. |
| 5,492,672 | A | 2/1996 | Childers et al. |
| 5,868,999 | A | 2/1999 | Karlson |
| 2002/0085950 | A1 | 7/2002 | Robitaille et al. |

FOREIGN PATENT DOCUMENTS

| CA | 2270512 | 10/2000 |
|---|---|---|
| CA | 2298165 | 8/2001 |
| CA | 2466307 | 5/2003 |

*Primary Examiner*—Elizabeth L McKane
(74) *Attorney, Agent, or Firm*—Diederiks & Whitelaw, PLC (57) ABSTRACT

A method for increasing a relative humidity in an enclosed space (10) comprising a plurality of graduated steps. The relative humidity is increased from a first relative humidity to a target relative humidity. The method is issued to humidify a chamber (10) wherein a sterilization process using a humidified ozone takes place. The method is carried out by an apparatus for effecting the humidified ozone sterilization comprising a processor programmed to effect humidification in a plurality of gradual steps.

17 Claims, 4 Drawing Sheets

APPARATUS AND METHOD FOR HUMIDIFYING A STERILIZATION CHAMBER

FIELD OF THE INVENTION

The invention relates to methods of humidification such as methods of humidifying a sterilization chamber in a sterilization process using humidified ozone as the sterilant or sterilizing agent.

BACKGROUND OF THE INVENTION

Sterilization is the destruction of any virus, bacteria, fungus or other micro-organism, whether in a vegetative or in a dormant spore state. Conventional sterilization processes for medical instruments have involved high temperatures (such as steam and dry heat units) or toxic chemicals (such as ethylene oxide gas, EtO). Steam sterilization with an autoclave has been the time-honoured method of sterilization. It is fast and cost effective. However, the autoclave destroys heat-sensitive instruments. Thus, since more and more heat-sensitive instruments such as arthroscopes and endoscopes are used in medical treatment, other types of sterilization are needed, especially cold sterilization.

Ethylene oxide may be used to cold sterilize heat-sensitive instruments. However, It has now been deemed by national health and safety organizations to be carcinogenic and neurotoxic. It also poses flammability problems and is thus usually used in combination with chlorofluorocarbons (CFC's) which themselves are now undesirable. Further, sterilization with ethylene oxide takes 14 to 36 hours.

A more efficient, safer, and less expensive sterilization agent is ozone ($O_3$). Ozone, especially humidified ozone, is a sterilizing gas. Ozone can easily be generated from oxygen, especially hospital grade oxygen. Oxygen is readily available in the hospital environment, usually from a wall or ceiling oxygen source, or, if mobility is required, from a portable "J" cylinder of oxygen. Ozone is widely used in industry as an oxidising agent to bleach paper pulp, treat drinking water, and sterilize sewage water and food products. The amounts (concentrations) of ozone required in the sterilization gas for water purification are low, generally less than 40 mg/l (milligram per liter). However, higher concentrations, combined with critical humidity levels, are required to make ozone an effective sterilant of micro-organisms. Those high concentrations of ozone gas have to be combined with critical levels of humidity. The sterilization efficiency of ozone increases rapidly with increased relative humidity. A high relative humidity is required for ozone to penetrate the protective shells of micro-organisms. The presence of water vapour will also accelerate ozone reactions with organic substances. Sufficient relative humidity further helps the penetration of sterilization packaging by ozone.

Sterilization with ozone is more efficient and quicker than with EtO and requires few changes in user habits. Moreover, ozone-based processes are compatible for use with current packaging, such as sterile pouches and rigid containers.

Ozone sterilization requires substantially no aeration or cooling down of sterilized instruments which can be used immediately following sterilization. This allows hospitals to reduce the cost of maintaining expensive medical device inventories. Ozone sterilization offers several other advantages. It produces no toxic waste, does not require the handling of dangerous gas cylinders, and poses no threat to the environment or the user's health. Stainless-steel instruments and heat-sensitive instruments can be treated simultaneously, which for some users will obviate the need for two separate sterilizers.

U.S. Pat. No. 3,719,017 discloses the use of a mixture of ozone gas with a very fine water mist in a sealed plastic bag container which contains an article to be sterilized. The method involves repeated evacuation and refilling of the plastic bag with a mixture of ozone gas and a very fine water mist. The air in the bag is exhausted and replaced with a pressurised mixture of ozone and water mist. Upon encountering the much lower pressure within the bag, the water particles from the pressurised mixture explode, forming a water mist. However, this system cannot generate a sufficiently high water vapour concentration to provide the high relative humidity required for thorough sterilization (at least 85% relative humidity).

U.S. Pat. No. 5,069,880 describes a device capable of generating a relative humidity of 85%. In the apparatus the ozone is bubbled through a water bath to increase the water content of the gas. Although ozone at 85% humidity can kill most micro-organisms, it does not meet the "worst case scenario" stipulated in North American standards. Moreover, the device is unable to generate humidity levels higher than 85%. In, addition, injecting ozone while humidifying the chamber increases the contact time of the ozone with the instruments to be sterilized, which may result in oxidation damage to the instruments.

A minimum relative humidity level of 90% (95%±5%) is required to meet North American standards set by agencies such as the Food and Drug Administration and Health Canada.

Water evaporates at 100° C. at atmospheric pressure (1013 mbar or 760 Torr). Thus, various prior patents (see Faddis et al., U.S. Pat. Nos. 5,266,275; 5,334,355; and 5,334,622) teach sterilization systems wherein water is heated to above the boiling point to evaporate the water for injection into the ozone-containing gas produced by an ozone generator. The steam is heated to 120° C. Thus, the vapour upon injection into the ozone-containing gas will have a temperature close to 100° C. However, since the decomposition of ozone increases exponentially with temperature in the range of 20 to 300° C., injecting the water vapour at a temperature of about 120° C. leads to premature ozone decomposition. As a result, the effective ozone concentration in the gas produced by the ozone generator is reduced, thereby requiring significantly increased treatment times and the generation of larger amounts of ozone gas for each sterilization cycle. Thus, a more efficient and effective sterilization apparatus is desired for the sterilization of ozone at a relative humidity of above at least 90%.

U.S. patent application Ser. No. 10/005,786 (filed on Nov. 8, 2001 which is a continuation-in-part application of U.S. patent application Ser. No. 09/310,695 which was filed on May 12, 1999 and is now abandoned), which is hereby incorporated by reference, addresses these problems by applying a vacuum pressure to lower the boiling point of water below the temperature inside the sterilization chamber. Thus the teachings of this application provide an effective sterilization process.

As taught in this prior application, it is preferred to repeat the sterilization cycle at least once to give greater assurance of effective sterilization. Thus, after loading the sterilization chamber with the articles to be sterilized (such as medical instruments), a sterilization cycle includes exposing the articles to the humidified ozone sterilant and then removing the sterilant. Repeating this cycle thus includes exposing the articles again to humidified ozone sterilant and removing the sterilant.

However, as mentioned above, in order to be sure of sterilization using ozone, the humidity should be at least 90% (95%±5%). Consistently achieving such high humidity levels has proved difficult. The sterilization chamber is in communication with a source of water vapour, for example, a water reservoir. As taught in U.S. patent application Ser. No. 10/005,786 mentioned above, a reduction in pressure will cause water in the reservoir to evaporate. However, this evaporation leads to cooling of the reservoir. Also, condensation of water vapour in the chamber tends to heat the chamber.

Any increase in the chamber temperature increases the quantity of water vapour required to reach the target humidity. Attempts to speed the process involve large thermal energy inputs, for example excessive heating of the water reservoir. This thermal energy eventually reaches the chamber and results in a temperature increase in the chamber which increases the quantity of water vapour needed for a given relative humidity. Thus achieving a high relative humidity with the consistency and accuracy needed to ensure complete sterilization is challenging.

SUMMARY OF THE INVENTION

It has now been found that effecting the humidification in a plurality of graduated steps or stages can provide a consistent and accurate way to reach a particular value of relative humidity, especially high relative humidity values such as those required for ozone sterilization.

According to one aspect of the present invention there is provided in a process for increasing a relative humidity in an enclosed space from a first relative humidity to a target relative humidity by increasing the relative humidity in a plurality of graduated steps.

According to another aspect of the present invention there is provided a process for humidifying an atmosphere in a sterilization chamber to a target relative humidity, the process comprising the steps of a) providing an amount of water in a water reservoir at a temperature $T_s$ at or above a temperature of the chamber atmosphere $T_c$; b) reducing a pressure in the chamber to a value below the boiling point of water at the reservoir temperature $T_s$; c) bringing the reservoir into fluid communication with the chamber for exposing the water in the reservoir to the reduced pressure in the chamber for a preselected exposure time so that water in the reservoir is boiled and to allow resulting water vapour to enter the chamber; and repeating at least steps b) and c) a plurality of times, wherein at least one of the amount of water and the exposure time are controlled such that the relative humidity in the chamber progressively increases with each repetition until the target humidity is reached.

According to another aspect of the present invention there is provided a method of humidifying an enclosed space to a target relative humidity, the method comprising a plurality of humidification stages $S^x \ldots S^u$, wherein x is an integer from 1 to n and each x represents an individual stage, each said stage having a corresponding water vapour pressure $h_x, \ldots h_n$, and $h_u$ representing the water vapour pressure corresponding to the target relative humidity, each stage $S_x$ including the steps of a) supplying water vapour from a water vapour source to the enclosed space to increase the water vapour pressure in the space to at least the value $h_x$ corresponding to said stage $S_x$ b) disconnecting the source from the space for a predicted equilisation period, and c) repeating steps a) and b) until said water vapour pressure $h_n$ is reached in the space.

According to another aspect of the present invention there is provided an apparatus for sterilization with humidified ozone, the apparatus comprising a sterilization chamber, a reservoir to hold water while in operation, to provide a source of water vapour to humidify the ozone, a conduit in fluid communication between the reservoir and the sterilization chamber, a valve in the conduit to open and close the conduit, a first heating means to control the temperature of the chamber, a second heating means to control the temperature of the reservoir, a first temperature sensing means to monitor the temperature of the sterilization chamber, a second temperature sensing means to monitor the temperature of the reservoir, a pressure sensing means to monitor the pressure in the chamber, vacuum means to reduce the pressure in the chamber, a processor to control the first and second heating means in response to information from the first and second temperature sensing means and the pressure sensing means, wherein the processor is programmed to effect a humidification of the sterilization chamber in a plurality of stages.

The invention will be described with reference to an ozone sterilization process using humidified ozone. However it will be understood that the humidification process according to the invention is applicable to any process which requires accurate humidification.

In a sterilization process, the space to be humidified would be the sterilization chamber.

In the preferred use of the stage-wise humidification in a humidified ozone sterilization process, the process would normally additionally include other steps such as placing a load of instruments to be sterilized into a sterilization chamber and injecting ozone into the chamber.

Throughout this description, units of pressure will be variously indicated in mbar, Torr, atmospheres or ¼ Torr. 1 atmosphere equals 760 Torr or 1013 mbar.

One or more ventilating cycles can be added to the preferred method for removing the remaining ozone and humidity from the sterilization chamber.

BRIEF DESCRIPTION OF THE DRAWINGS

The invention will be described in more detail in the following by way of example only and with reference to the attached drawings wherein.

DETAILED DESCRIPTION OF THE PREFERRED EMBODIMENT

Preferably the source of water vapour is a reservoir of water in a humidifier chamber or humidifier unit. The temperature of the water vapour source or the water in the reservoir may be represented as $T_s$. The temperature of the space to be humidified or the sterilization chamber may be represented by $T_c$. Preferably there is at least one heating means for each of the sterilization chamber and the reservoir. Such heating means may be referred to as a first and second heating means. Preferably the reservoir water is at the same temperature as or a higher temperature than the temperature of the sterilization chamber, that is, $T_s \geq T_c$. The difference in temperatures may be expressed as $\Delta T$ (delta T) so that $T_s - T_c = \Delta T$ and thus $\Delta T \geq 0$. Preferably the temperature difference $\Delta T$ is from 0 to 10° C. more preferably from 0 to 7° C. and particularly from 0 to 3° C. Maintaining the reservoir water at a higher temperature encourages evaporation of water vapour and encourages the vapour to flow to the sterilization chamber and discourages loss of humidity from the sterilization chamber by recondensation in the reservoir.

The number of stages to be used to complete the humidification, or to achieve the target relative humidity, is widely variable. A large number of stages could be used. Selection of the number of stages will depend on the accuracy of the equipment used and a preference to complete the humidification as quickly as possible without adversely affecting the ability to accurately obtain the desired relative humidity. Thus, out of convenience, humidification would preferably be achieved in less than 50 stages, more preferably from 3 to 30, or from 5 to 27.

In a presently preferred embodiment, a processor is programmed with information corresponding to 27 stages (shown hereafter in Table 1) although the last 10 to 15 stages are included in case the sterilization chamber temperature $T_c$ increases beyond the preferred temperature (thus requiring a higher water vapour pressure to achieve the same value of relative humidity) but they are not always required. Similarly, depending on the circumstances, it is sometimes possible to achieve up to 60%, or even up to 80% of the target Relative Humidity in a first stage, so that in the 27 stages (shown hereafter in Table 1), the first few stages, preferably up to 5 stages (which in a preferred embodiment would correspond to a water vapour pressure of 112×¼ Torr) may be combined into a first single stage. It is preferred to reach a water vapour pressure of about 80×¼ Torr in a first stage.

If it is attempted to proceed too quickly or in too few stages, condensation will tend to occur in the sterilization chamber which will increase the chamber temperature which will in turn impose a need for a greater amount of water vapour to reach the target relative humidity. Such an unfavourable sequence can become out of control so that the target relative humidity cannot be reached. Thus it is preferred to take at least 5 to 10 stages, preferably 10 or more, to reach the target relative humidity.

Even more care should be taken in the later stages to allow the system to stabilize. Thus it is preferred that at least the last 10 stages, preferably the last 5 stages, particularly the last 3 stages should be effected in such a way that the increase in water vapour pressure achieved in the sterilization chamber is in a small increment for each stage, for example from 0.1 to 5 Torr, preferably 0.1 to 3 Torr and particularly from 0.25 to 1 Torr. In a preferred embodiment the last 10 or more stages are pressure increments of about 0.5 to 1 Torr.

The humidification thus should proceed in graduated stages, preferably in fairly discrete stages. Thus in a given stage, after reducing the pressure in the water reservoir (for example, by evacuating the sterilization chamber and opening a valve to put the reservoir and sterilization chamber in fluid communication) the boiling point of the water in the reservoir will be reduced below the actual temperature of the water, thus the water will boil, water vapour will be formed and can thus travel or flow to the sterilization chamber. The evaporation will cause the temperature of the water reservoir to drop. It is thus necessary to heat the reservoir to return the temperature $T_s$ back to or above the chamber temperature $T_c$. During this re-heating, it is preferred to close the valve in the conduit joining the chamber to the reservoir. Thus the reheating becomes a preparation for the next stage. Thus the valve is closed, disconnecting the reservoir or water vapour source from the chamber for a time sufficient to adjust either the chamber temperature, or preferably the reservoir temperature, to return $T_s$ to the preferred value of $T_c$ or above.

In order to better control the stages, it is preferred that there is a temperature sensing means to monitor the temperature of the water in the reservoir. A temperature sensing means is also preferred to monitor the chamber temperature. Thus if the chamber temperature sensing means is referred to as a first temperature sensing means, then the reservoir temperature sensing means may be referred to as a second temperature sensing means or temperature sensing device. A suitable device is a Resistance Temperature Dependent sensor (RTD) such as a class B type sensor commercially available from Omega Temperature. This type of device has a resolution of 100 degrees, a standard deviation of 0.00385 and a tolerance of 0.3 degrees which means that it can measure a temperature to an accuracy of within about ±0.15 degrees. The temperature sensing means are preferably connected to a processor, computer or programmable logic controller so that the temperature data can be fed to the processor. The RTD provides temperature measurements to a processor which can adjust the heating accordingly, by means of a Proportional Integral Differential (PID) function of the Programmable Logic Controller (PLC). The heating means are connected so as to be under control of the processor. Thus by also providing pressure sensing means to monitor the pressure in the chamber, and connecting this also to the processor, the humidification stages can be automated. The processor may be programmed with a table of target values of temperatures, pressures and times, and instructed to proceed with the humidification according to a pre-programmed sequence in accordance with the table.

As mentioned above, condensation in the chamber will tend to increase the chamber temperature and will run the risk of losing control of the humidification. Therefore, the number of stages and the corresponding water vapour pressure values are selected to reduce the risk of condensation of water vapour in the sterilization chamber, preferably to avoid substantially any condensation in the chamber.

In the preferred use of the stage-wise humidification in a humidified ozone sterilization process, the process would normally additionally include other steps such as placing a load of instruments to be sterilized into a sterilization chamber and injecting ozone into the chamber.

Figure 1:
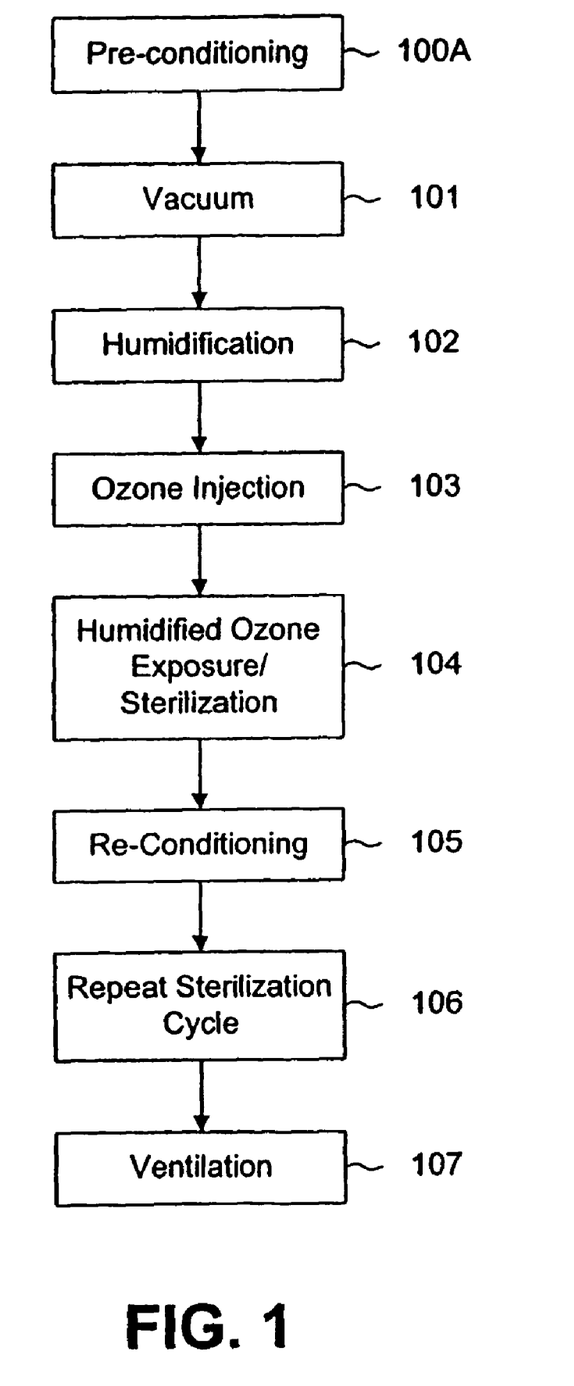
FIG. 1 is a flow diagram of a method in accordance with the invention.
Figure 2:
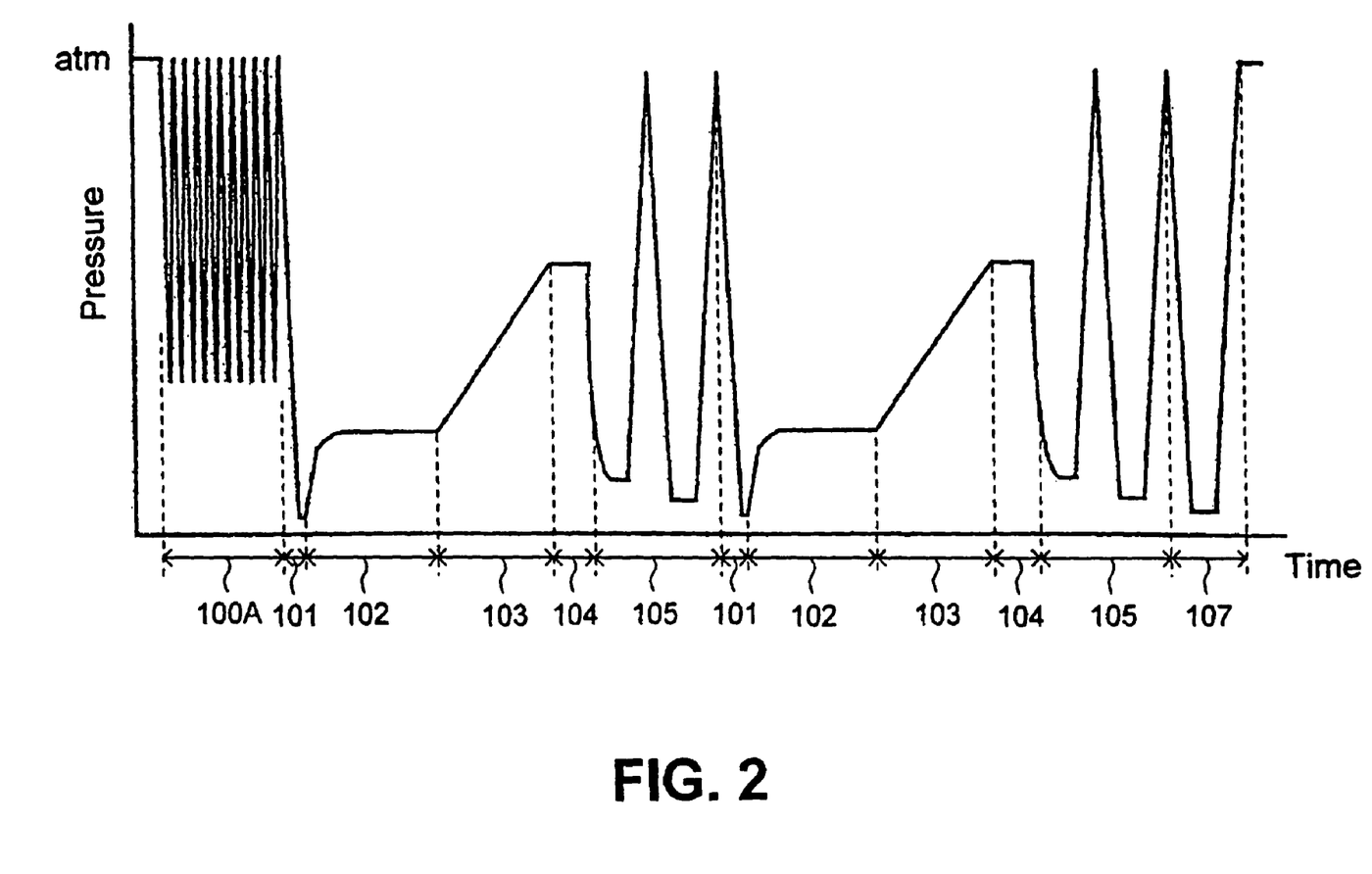
FIG. 2 is a graph to illustrate the sequence of steps in a method in accordance with the invention by plotting pressure against time.

As can be seen from FIGS. 1 and 2, the process can be regarded as including six or seven basic steps, some of which may be repeated in a second sterilization cycle.

FIG. 1 is a schematic representation of a sterilization process according to the invention, showing the steps of the process in sequence. FIG. 2 is another representation of a process according to the invention. FIG. 2 illustrates the process by showing the various steps as a function of the pressure. Thus the vertical axis shows the pressure, with atmospheric pressure represented at the top end of the vertical axis and zero pressure (or complete vacuum) at the bottom end of the vertical axis. The horizontal axis represents the sequence of steps in the process from left to right and thus corresponds to elapsed time, although not necessarily to any scale, but only for the purpose of illustration.

Since the present invention is mainly concerned with the humidification step, it will be understood that details of other process steps are in the nature of preferred features which are not essential to the broadest aspects of the invention.

As shown in FIGS. 1 and 2, preferably the sterilization is preceded by a conditioning step, indicated as step 100A. This step may also be referred to as a preconditioning step. In this step, after inserting the articles to be sterilized in a sterilization chamber, the chamber is sealed.

Generally, it is preferred to effect the sterilization at a target temperature in the range of from about 25 to 40° C., more preferably from about 30 to 36° C. and especially at around 30° C., for example at 30.8° C. The walls of the chamber are preferably maintained at around this sterilization temperature. Since this is above usual room temperature, it is preferred to successively fill and empty the chamber, with ambient air, in a succession of pulses. This pulsing helps stabilize the conditions in the chamber and helps bring any load (instruments to be sterilized) to the preferred chamber temperature. This is represented by the peaks and troughs shown in FIG. 2 in the left-hand portion of the graph indicated as 100A, which represents the pre-conditioning step. The peaks represent a pressure of around atmospheric pressure and thus represent at least partially filling the chamber with ambient air. The troughs represent reduced pressure or evacuations of the chamber. Room temperature is usually around 18 to 22° C. so to reach a target temperature of, for example, 30° C., the air must be heated. The walls of the sterilization chamber are preferably heated. Thus by pulsing a quantity of air into and out of the chamber, the temperature of the air and the temperature of the load (any instruments in the chamber for sterilization), approaches the target chamber temperature of around 30° C. Generally it is preferred that a reduced pressure in the range of from about 350 to about 450 Torr, more preferably about 250 Torr, is used to evacuate the chamber in each of the evacuation pulses in this pre-conditioning step. It is preferred that the ambient air load is pulsed from 7 to 16 times, more preferably ten times. However, the number of such pulses may be increased or decreased to bring the load of ambient air to a satisfactory temperature.

Any inert gas may be used as the gas in the pre-conditioning step. The choice of gas will be governed by costs or by consideration of whether it will interfere with the sterilant in the subsequent sterilization steps. In later steps, it is preferred to avoid using air since the nitrogen which it contains may form harmful substances, such as nitrogen oxides as a result of the powerful oxidizing capacity of ozone. Such nitrogen oxides may then form traces of nitric acids with any water vapour and may thus damage parts, such as metal parts, of articles to be sterilized. However, in this pre-conditioning step, air can be used, although oxygen would be preferred.

The next step is the vacuum step and is indicated as 101 in FIGS. 1 and 2. In this step, gaseous contents of the sterilization chamber are evacuated. It is preferred to use a deep vacuum, generally in the range of from about 5 to 0.5 Torr, more preferably about 2.5 to 0.5 Torr, more particularly, less than 1.25 Torr to remove as much of the gaseous contents as possible. It is preferred to apply this pressure for a time in the range of from about 30 seconds to 5 minutes, more preferably about a minute to allow the pressure to stabilize within the chamber, especially considering that the articles to be sterilized may well include containers and pouches.

The next step is the humidification step and is indicated as 102 in FIGS. 1 and 2. This step is to provide the sterilization chamber with the humidity required for sterilization. Water from a water reservoir is evaporated and introduced into the chamber as water vapour until the relative humidity is equal to or above the target value. It is preferred that the relative humidity during sterilization is at least above 90%, preferably 95% or higher. It is preferred that after the target humidity is reached, conditions are maintained to stabilize and equilibrate the conditions throughout the chamber and the articles in the chamber. Preferably conditions are maintained for a time in the range of from about 10 to 50 minutes, more preferably for at least 30 minutes.

Relative humidity is a percentage and represents the water vapour present as a percentage of the theoretical maximum water vapour possible at a given temperature. Thus a relative humidity of 100% represents the theoretical maximum water vapour pressure at a given temperature. Since warm air holds more water than cool air, an increase in temperature requires an increase in water vapour to maintain 100% relative humidification.

The humidification step or humidification phase is a complex process achieved by graduated steps or increments.

The means of humidification, or humidifier, includes a source of water, preferably contained as a reservoir, to provide the water vapour for humidification. In one embodiment the source of water is provided by a cylinder in which there is a known volume of water (in a process using a 125 liter sterilization chamber, a volume of 500 mls or less is preferred, in particular, a volume of about 300 mls±10 mls) which is sufficient to provide the required relative humidity under the process conditions.

The water in the water reservoir is preferably heated to a temperature which is equal to or above the temperature of the sterilization chamber. If the temperature of the water reservoir is less than the chamber, then as the humidification progresses, a point will be reached where no more water will evaporate from the reservoir even though the target relative humidity has not been reached. A lower temperature in the reservoir will thus function as a "cold spot" which encourages condensation rather than evaporation.

The water reservoir or source, is in fluid communication with the sterilizing chamber by means of a conduit which may be referred to as a water vapour diffuser. The conduit preferably includes a valve by which fluid communication between the chamber and the source can be disconnected in an "off" position or re-connected in an "on" position. Preferably, this conduit, or water vapour diffuser, is also kept at a temperature above the temperature of the chamber. The temperature of the water vapour diffuser is also preferably monitored, by a sensor such as an RTD sensor described above, and the measured temperature information sent to a processor so that appropriate heating adjustments may be made to maintain a desired temperature. Preferably, the water vapour diffuser is maintained at about 3° C. (±0.5° C.) above the temperature of the water source.

Since the water source is also usually kept above the temperature of the chamber during the humidification step, this means that the water vapour diffuser may often be some 7 or 8° C. higher that the chamber.

Before starting the humidification stage, the water source is heated to a temperature corresponding to the average temperature of the sterilization chamber. As mentioned above, a preferred sterilization chamber temperature is around 30.8° C.

Just before the HS (humidification step) a vacuum is applied to the sterilization chamber to reduce the pressure in the chamber, preferably to about ¾ Torr. At this pressure, the boiling point of water is −15° C. Thus, if the water source or reservoir is at or above the preferred chamber temperature of 30.8° C., when the valve in the water vapour diffuser is opened, the water source will be in fluid communication with the sterilization chamber and water will evaporate from the reservoir and enter the sterilization chamber.

As mentioned above, in order to consistently and precisely obtain a particular relative humidification valve, especially the high values of 90% or higher, which are preferred (and sometimes required) for efficient ozone sterilization, there are many difficulties to overcome.

When the water reservoir, which is at a temperature of, for example, 30.8° C. is exposed to the low pressure of the chamber at for example, 5/4 Torr, by means of opening the valve, water will immediately evaporate and the resulting water vapour will enter the sterilization chamber. However, the evaporation has a cooling effect which will also lower the temperature of the water source.

In practice, at the start of the humidification step, when the valve is opened, although water vapour enters the sterilization chamber, the quantity of water vapour which enters the chamber is insufficient to produce a high relative humidity especially the relative humidity values at or above 90% which are required for ozone sterilization. Further, in practice, the Sterilization chamber has "cold spots". These are locations within the chamber which are at a lower temperature than the average chamber temperature or lower that the target temperature. Such "cold spots" may be provided by components of the load (the medical instruments to be sterilized) within the Sterilization chamber which may not have reached the target temperature, or they may be provided by structural limitations of the chamber itself (such as supporting members to support the configuration of the chamber which members cannot be directly heated, but only heated indirectly from the other chamber components). Such "cold spots" may induce some condensation. Any condensation in the chamber will tend to increase the temperature of the chamber (because of the thermal energy emitted by the condensation process). Any increase in chamber temperature will increase the water vapour needed to reach the desired relative humidification. Further, in some systems, the chamber may not be provided with any cooling means and thus quickly reducing the temperature to the preferred target temperature value, may not be possible. Further, simply continuing to heat the water source to obtain the desired water vapour content will tend to exacerbate any problems such as those caused by condensation on "cold spots".

According to the invention the humidification preferably proceeds in a number of graduated steps which may be indicated as a series $S_1, S_2, S_3 \ldots S_n$ in which n indicates the number of steps. Thus an intermediate step in this series may be represented as $S_x$ in which x is the number of the step between 1 and n. For each of the steps there is a corresponding water vapour pressure $h, h_2 \ldots h_n$, which represents a target water vapour pressure value for the corresponding stage. Thus an intermediate step $S_x$ would have a corresponding water vapour pressure value $h_x$.

If both the temperature of the chamber and the water vapour pressure in the chamber are known, then the relative humidity may be calculated. At a temperature of 30.8° C., for 100% relative humidity, the water vapour pressure is 34 Torr.

As mentioned above, it is preferred that the temperature of the water source is kept above the chamber temperature. This temperature differential (being the difference in temperature between the water source and the Sterilization chamber) may be represented as $\Delta T$ (delta T). Further, it is preferred that the temperature differential is selected according to each individual humidification stage. Thus, for example, the temperature differential may be chosen to be higher in the earlier stages and less in the later stages or vice versa. In practice, a series of suitable temperature differentials $dt_1, dt_2, \ldots dt_n$ each corresponding to the humidification stage of the same number, is selected for optimum control of the humidification. An intermediate stage $S_x$ will thus have an associated $\Delta T$ value of $\Delta T_x$. Towards the latter stages of the humidification, the temperature difference will preferably level out to avoid overheating the water and causing the chamber temperature to increase undesirably.

A preferred humidification step may have many individual stages. The following Table 1 shows 27 possible stages with corresponding pressure and temperature differential values.

TABLE 1

Correspondence table between humidification stage, water vapor pressure set point, and Delta T applied to the humidifier temperature set point

| Humidification stage | Water vapor pressure Set point (1/4 Torr) | Delta T (1/100° C.) |
|---|---|---|
| 1 | 0 | 0 |
| 2 | 80 | 75 |
| 3 | 100 | 125 |
| 4 | 108 | 175 |
| 5 | 112 | 225 |
| 6 | 116 | 275 |
| 7 | 120 | 325 |
| 8 | 122 | 375 |
| 9 | 124 | 433 |
| 10 | 126 | 485 |
| 11 | 128 | 533 |
| 12 | 130 | 570 |
| 13 | 134 | 585 |
| 14 | 138 | 600 |
| 15 | 142 | 600 |
| 16 | 146 | 600 |
| 17 | 150 | 600 |
| 18 | 154 | 600 |
| 19 | 158 | 600 |
| 20 | 162 | 600 |
| 21 | 166 | 600 |
| 22 | 170 | 600 |
| 23 | 174 | 600 |
| 24 | 178 | 600 |
| 25 | 182 | 600 |
| 26 | 186 | 600 |
| 27 | 190 | 600 |

In Table 1 above, the left hand column gives the number of the individual humidification stage, the middle column gives the associated water vapour pressure for that stage (in the table, the pressure is given in units of 1/4 Torr) and the right hand column indicates the preferred temperature differential for that particular humidification stage, that is, the difference in temperature between the chamber and the water source (the temperatures in table 1 are given in units of hundredths of a degree centigrade).

This table of values is programmed into a processor (such as a computer, for example the PLC), so that the parameters can be controlled automatically in response to the particular conditions, such as chamber temperature and pressure, as measured by the system components.

Looking at Table 1 in more detail, at the start of the humidification step the water source is at approximately the same temperature as the chamber and the chamber has just been evacuated (at least preferably to a pressure of 5/4 Torr). This represents stage 1 with corresponding water vapour pressure of 0 and temperature differential (Delta T) of 0. The valve is then opened and water evaporates from the source to enter the sterilization chamber as water vapour. The valve is shut and the water source is heated to 75/100° C. above the chamber temperature. The valve is now opened again. This is now stage 2 of the humidification, and when the pressure in the chamber reaches 80×1/4 Torr (as shown in Table 1 as the pressure corresponding to stage 2) the valve is closed and the water source is heated to 125/100 degrees above the chamber temperature and the valve is opened for stage 3 until the corresponding pressure of 100×¼ Torr is reached.

The process is repeated through all the stages until the relative humidity in the chamber is calculated to be equal or above the target relative humidification.

As mentioned above, for a chamber temperature of 30.8° C., a relative humidity of 100% is represented by a water vapour pressure of 34 Torr. However, during the process, the chamber temperature may exceed the preferred temperature, and thus a higher water vapour pressure will be needed to give the same relative humidity value. The chamber temperature is regularly monitored and the value is provided to the processor. The processor keeps repeating the humidification stages from $S_1$ to $S_2$ to $S_3$ etc. until the water vapour pressure inside the chamber (for the actual chamber temperature) corresponds to the target relative humidity.

Table 1, which is programmed into the processor, thus has a sufficient number of humidification steps, with corresponding pressure and temperature information, to ensure that even when the chamber temperature increases beyond the preferred temperature, the processor has sufficient information to ensure reaching the target relative humidification.

It is also preferred to run the humidification step for a minimum time to further assist in ensuring proper humidification.

It is preferred that the target humidity is reached within 10 to 31 minutes. Thus, when the water vapour pressure set point is reached (which is 34 Torr±0.25 Torr for a chamber temperature of 30.8° C.) a "humidification plateau" is allowed for from 10 minutes to 1 hour, preferably for at least about 31 minutes. During the humidification plateau, the water vapour diffuser is kept at 37° C. to avoid any condensation in the diffuser and the valve is kept open to allow any additional water vapour which may be needed to maintain the target relative humidification (since, in practice, the chamber temperature may increase during the humidification plateau).

The minimum humidification time is preferably 50 minutes. If the minimum water vapour pressure is reached in less than 19 minutes, the "humidification plateau" is extended beyond the preferred 31 minutes to ensure a total humidification time of at least 50 minutes. Otherwise, if the minimum water vapour pressure takes longer that 19 minutes to reach, the "humidification plateau" is still kept for 31 minutes, so the total humidification step will last longer than the minimum 50 minutes.

The temperature of the sterilization chamber is monitored regularly. The temperature may be measured by using a device such as the RTD sensor discussed above. It is preferred to measure the chamber temperature indirectly. Since the mass of the gas in the chamber is so small, direct measurement would be inaccurate. The chamber temperature is therefore obtained by averaging measurements of the chamber back wall, top wall and bottom wall.

$$\text{Thus } T_{AV} = \frac{[T_R + T_T + T_B]}{3}$$

Where $T_{AV}$=Average chamber temperature $T_R$=Temperature of rear wall $T_T$=Temperature of top wall and $T_B$=Temperature of bottom wall The temperature controls are summarized as follows.

While the sterilizer is not in the Humidification phase: the water vapor diffuser temperature set point is 37° C.±0.5° C.; the Humidifier heater set point is: [Average Chamber Temperature]; and the chamber door heater set point is [Average Chamber Temperature].

During the Humidification phase: the Humidifier heater set point is [Average Chamber Temperature]+[Delta T]$_{curve}$; the water vapor diffuser temperature set point is: [T$_{RTDHumdifier}$]+[3° C.±0.5° C.]; and the chamber door heater set point is [Average Chamber Temperature].

The values for [Delta T]$_{curve}$ are values obtained from Table 1.

Thus there is what may be referred to as a thermal inertia. That is, thermal energy added to the system, for example the heat which is applied to the water source, takes time before it is distributed throughout the whole system, even to the perimeters of the system.

Figure 4:
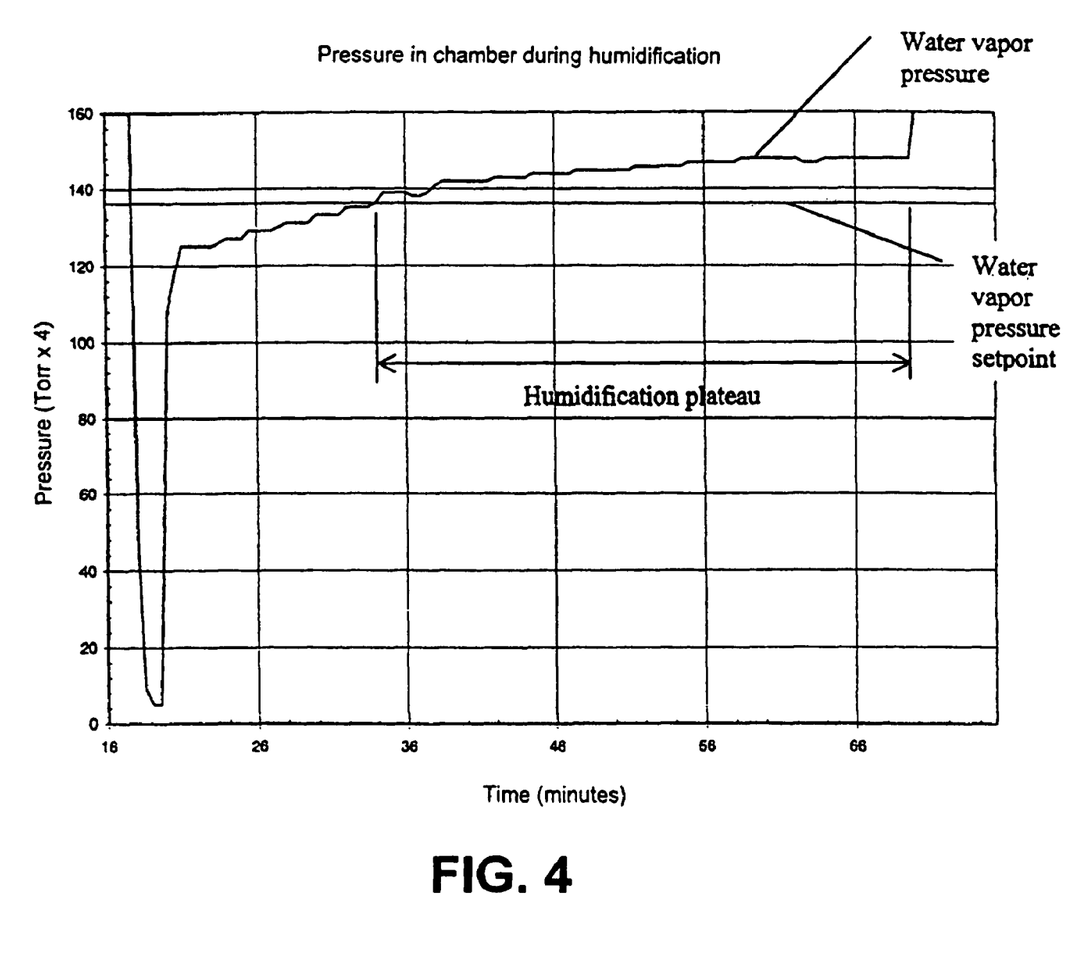
FIG. 4 is a graph showing progress of a humidification step according to the invention.

FIG. 4 shows the progress of a humidification using graduated steps. The vertical axis shows the pressure in the Sterilization chamber in units of ¼ Torr. The horizontal axis shows the time. The target water vapour pressure at the preferred chamber temperature of 30.8° C. is about 136×¼ Torr (which is 34 Torr). After this pressure has been reached, the valve is kept open so that the water source and the chamber are in fluid communication during the "humidification plateau". The target water vapour pressure of 136×¼ Torr is shown on the figure as the water vapour set point. After reaching the set point, the "humidification plateau" is maintained for 31 minutes as shown in the figure. It can also be seen from the figure that in the last 5 to 10 minutes of the humidification plateau, there are virtually no further increases in pressure, which shows that the conditions in the chamber have stabilized.

After the humidification step, the next step is an ozone injection step which is represented as step 103 in FIGS. 1 and 2. Ozone is generated by an ozone generator. It is preferred to monitor the ozone produced by the generator to ensure that a sufficient quantity of ozone will be introduced to the sterilization chamber. Thus preferably the ozone generator is activated before the end of the humidification step so that sufficient ozone is being generated by the time it is required at the end of the humidification step. For a sterilization chamber of about 125 Liters, an ozone generation of between 160 and 200 mg/L at normal temperature and pressure (NTP) from the generator is preferred. Preferably, used ozone and unrequired ozone is catalytically destroyed (by conversion to oxygen) before expelling it to the atmosphere to avoid pollution.

A suitable ozone generator produces ozone from oxygen (preferably extra-dry medical grade oxygen) which is submitted to an electrical field produced inside the generator, suitably at a high frequency voltage of about 10,000 volts peak to peak. The high voltage permits a corona discharge in the generator cells to convert the oxygen to ozone. Ozone is heat sensitive, so it is preferred to keep the ozone generator operation at around 2 to 4° C. to optimise ozone production. When ready, the ozone is introduced into the humidified chamber until the ozone in the chamber preferably reaches a concentration in the range of about 45 to 100 mg/L NTP, more preferably about 85 mg/L NTP. Coupled with the high humidity, this concentration is considered to be sufficient to achieve sterilization.

The next step is the humidified ozone exposure step which is indicated as step 104 in FIGS. 1 and 2. This step involves maintaining the level of ozone and humidity achieved from the previous steps for a time sufficient to achieve a satisfactory level of sterilization. A time period of from 5 minutes to 1 hour may be needed, although 15 minutes is preferred. This step completes the first sterilization cycle. In the interest of maximising the assurance of sterilization, it is preferred to repeat the sterilization with at least a second sterilization cycle, preferably including repeating at least steps 101, 102, 103 and 104.

The next step, is a re-conditioning step which is indicated as step 105 in FIGS. 1 and 2. The purpose of this step is to remove any condensed water. Preferably all, or substantially all of the condensed water is removed and preferably all, or substantially all of the water vapour is removed in this step. It is preferred that the amount of water removed is from about 75% to 100% by weight of all the water in the chamber, more preferably from about 80% to 100%. Thus this step may be regarded as a flushing or purging step to remove condensed water. It is also preferred that the temperature of the chamber is restabilized to the target temperature, for example, the preferred temperature of 30.8° C. The gaseous vehicle used for this purging or flushing step is preferably a gas which is inert in the context of the sterilization process. For example, some gases such as nitrogen and other gases, may form undesirable oxygenated products by contact with ozone and thus are preferably avoided. In this step, since it follows a previous sterilization cycle which has used ozone, it is preferred to avoid the use of air because of the high nitrogen content of air. The preferred gas for this step is oxygen, especially medical grade dry oxygen, which would usually be readily available in an environment in which the sterilization process of the invention would normally be used, such as a hospital. The reconditioning step preferably includes, or is preceded by, a vacuum step to remove humidity and ozone from the chamber. Preferably a vacuum in the range of about 20 down to 5 Torr, more preferably less than 10 Torr, is applied. Gaseous contents removed from the chamber are passed to a catalyst to convert any ozone to oxygen, for environmental reasons. It is preferred to maintain the low pressure such as the preferred pressure of 10 Torr for a period of time, preferably 2 to 3 minutes, to allow gaseous contents within articles in the chamber (especially articles having pouches and containers) to equilibrate with the rest of the chamber, to optimise removal. Medical grade oxygen is then introduced to the chamber. It is preferred that this re-conditioning step include at lease one repetition of the vacuum and oxygen injection steps to optimise the removal of all condensation.

The removal of condensed water may be referred to as a post-exposure step since it follows at least a first sterilization cycle and thus an exposure to the humidified ozone sterilant. However, it may be more appropriate to refer to it as a conditioning or re-conditioning step (since in preferred processes it may not be the first conditioning step and is intended to return the conditions within the chamber to conditions at least approximating those at the start of the sterilization).

When all the sterilization cycles have been completed, a ventilation step is effected, which is indicated as 107 in FIGS. 1 and 2. The purpose of this step is to remove ozone and water vapour before the sterilization chamber is opened and the sterilized articles are removed.

It will be readily understood by a person skilled in the art that the sequence of some of the steps may be varied without compromising sterilization. Some steps might be effected simultaneously although the successive sequence described above is preferred.

Figure 3:
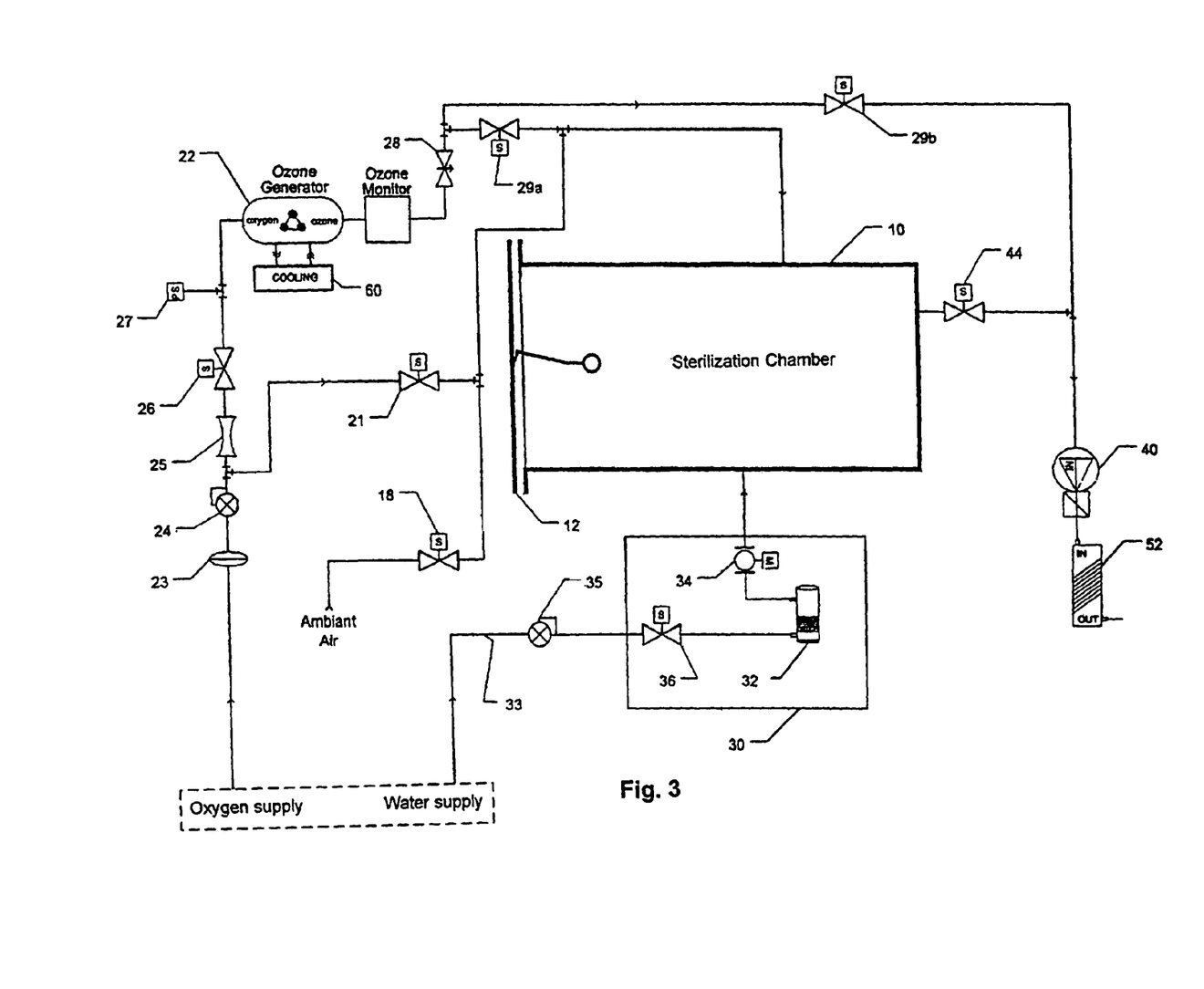
FIG. 3 is a schematic illustration of an apparatus suitable for use with the method of invention.

An ozone sterilizer apparatus, suitable for use with the method of the invention is illustrated schematically in FIG. 3. Medical quality oxygen is subjected in an ozone-generating unit including an ozone generator 22 to an electrical field, which partially converts the oxygen into ozone. The ozone is then fed into a humidified sterilization chamber 10 where it sterilises medical devices. The ozone is subsequently reconverted into oxygen using an ozone converting unit 52. The only residues left at the end of the sterilization cycle are oxygen and clean water vapour.

The apparatus includes a heated sterilization chamber 10 which can be sealed to contain a vacuum. This is achieved with an access door 12, which can be selectively opened for access into the chamber and which seals the chamber in the closed condition. The apparatus further includes an ozone generator 22 for supplying ozone-containing gas to the sterilization chamber, a humidifier arrangement 30 for supplying water vapour to the sterilization chamber, and a vacuum pump 40 (a suitable pump is a dry scroll vacuum pump manufactured by Anestiwata). The vacuum pump 40 is used for the application of a sufficient vacuum to the sterilization chamber 10 to increase the penetration of the sterilizing gas and to be able to boil water at a temperature below the temperature inside the sterilization chamber. The vacuum pump 40 in the preferred embodiment is capable of producing a sufficient vacuum in the sterilization chamber to lower the boiling point of water in the chamber below the temperature in the chamber. In the preferred apparatus, the vacuum pump is capable of producing a vacuum of 0.1 mbar. Ozone produced in the ozone-generating unit 22 is destroyed in an ozone converting unit 52 to which ozone-containing gas is fed either after passage through the sterilization chamber 10 or directly from the ozone-generating unit 22 through valve 29b. The ozone piping circuit includes an ozone converting catalyst (such as DEST 25, manufacturer TSO3). The ozone converting unit 52 is connected in series before or after the vacuum pump 40 to prevent ozone gas escaping to ambient air. The ozone decomposing material in the preferred catalyst is carulite. For economic and practical reasons, it is preferred to use a catalyst to decompose the ozone exhausted from the sterilization chamber 10. The catalyst destroys ozone on contact and converts it into oxygen with a certain amount of heat being produced. Catalysts of this type and their manufacture are well known to the person skilled in the art of ozone generators and need not be described in detail herein. Furthermore, other means for destroying the ozone contained in the sterilization gas will be readily apparent to a person skilled in the art. For example, the gas can be heated for a preselected time to a temperature at which the ozone decomposition is accelerated, for example, to 300° C.

The humidifier arrangement 30 includes a humidifier chamber 32 (such as HUM 0.5, manufacturer TSO3) sealed from ambient air and connected to the sterilization chamber 10 through a conduit and a vapour intake valve 34. The humidifier chamber 32 is equipped with a level control to ensure a sufficiently high water level (not shown). Water is directly supplied to the humidifier chamber 32 from a drinking or purified water supply connection. Water is supplied to the humidifier chamber 32 by way of a filter 33, a pressure regulator 35, and input valve 36. The water vapour produced in the humidifier chamber 32 enters the sterilization chamber 10 by way of a vapour intake valve 34.

The ozone-generating unit includes an ozone generator 22 (such as OZ, model 14a, manufacturer TSO3) of the corona discharge type, which is cooled to decrease the ozone decomposition rate, as is well known in the art. To achieve a good lethality rate in an ozone sterilization process, the ozone supplied in the sterilization chamber should be sufficient to obtain a concentration of 48 to 96 milligrams per liter, preferably 50 to 90 milligrams per liter. At these concentrations, the ozone generation is associated with a relatively high energy loss in the form of heat. Generally, about 95% of the supplied electrical energy is converted into heat and only 5% is used to produce ozone. Since heat accelerates the inverse transformation of ozone into oxygen, it must be removed as quickly as possible by cooling the ozone generator 22. The ozone generator in the apparatus is kept at the relatively low temperature of 3 to 6° C. by either an indirect cooling system with cooling water recirculation, or a direct cooling system with a refrigeration unit for cooling. The cooling system 60 is preferably kept at the temperature of 3 to 6° C. In the preferred embodiment, the cooling system is kept at 4° C. so that the ozone-containing gas generated by unit 22 is at the ambient temperature of around 20 to 35° C., preferably 30° C. Thus, the ozone-containing gas entering into the sterilization chamber for humidification and sterilization is kept at ambient temperatures of from 20 to 35° C. This means that ozone decomposition is kept to a minimum and that the sterilization process is more efficient.

The ozone-generating unit is preferably supplied with medical quality or medical grade oxygen. The apparatus can be connected to a wall oxygen outlet common in hospitals or to an oxygen cylinder or to any other source capable of supplying the required quality and flow. The supply of oxygen to the generator 22 takes place across a filter 23, a pressure regulator 24, a flow meter 25 and an oxygen shut-off valve 26. The generator is protected against oxygen over-pressure by a safety pressure switch 27. The ozone-oxygen mixture generated by the generator 22 is directed to the sterilization chamber 10 by a needle valve 28 and a mixture supply solenoid valve 29a. The mixture can also be directly supplied to the ozone converting unit 52 by way of a bypass solenoid valve 29b. In a preferred embodiment which includes a sterilization chamber of 125 liters volume, the pressure regulator 24 preferably controls the oxygen input at a flow rate of about 1.5 liters per minute. However, it will be readily apparent to the skilled person that other flow rates may be used depending on the make and model of the ozone generator 22 and the size of the sterilization chamber.

The apparatus in accordance with the invention preferably includes a closed circuit cooling system using no fresh water.

The vacuum in the sterilization chamber 10 is produced by the vacuum pump 40 and across the ozone converting unit 52 and the sterilization chamber drainage valve 44.

Operation

As mentioned above, the preferred sterilization method includes the following general steps as illustrated by the flow chart of FIG. 1. The medical instruments to be sterilized are sealed in sterile packaging containers or pouches such as generally used in the hospital environment and then placed into the sterilization chamber. The door of the sterilization chamber is closed and locked and the preconditioning phase is started by applying a vacuum to the sterilization chamber. Water vapour is admitted into the sterilization chamber to humidify the chamber contents. A mixture of ozone and oxygen is supplied to the chamber and the chamber maintained sealed for a preselected treatment period. Before repeating the sterilization cycle, a re-conditioning step is effected to remove any condensed water. Then the vacuum application and ozone supply steps are repeated at least once. To remove all remaining ozone in the sterilization chamber 10 when the sterilization cycle is completed a ventilation phase begins. After the ventilation phase is complete the door is unlocked and the sterilized material can be removed from the chamber.

Before the sterilization cycle begins, the humidifier chamber 32 is filled with water to an adequate level, which is sufficient to satisfy the requirements for the whole sterilization cycle. This is done by temporarily opening the water-input valve 36. Valve 36 remains closed for the whole remainder of the sterilization cycle. In the first phase of the sterilization cycle, intake valve 18, oxygen shut-off valve 26, mixture supply valve 29a, and mixture bypass valve 29b (optional) are closed and vapour intake valve 34, and chamber drainage valve 44 are opened. The sterilization chamber 10 is evacuated to a vacuum pressure of about 0.1 mbar. Water vapour inlet valve 34 closes when the absolute pressure in the sterilization chamber falls below 60 mbar. Once a pressure of about 1.0 mbar is achieved, the chamber drainage valve 44 closes and the vapour intake valve 34 opens to lower the pressure in the humidifier chamber 32 to the vacuum pressure in the sterilization chamber. That forces the water in the humidifier chamber to boil and evaporate and to enter the sterilization chamber 10 as water vapour. Shortly before the end of the humidification period (usually about 2 to 6 min. before the end of the humidification period), the ozone generator is activated. The flow of the oxygen/ozone mixture exiting the ozone generator is controlled by ozone mixture supply valve 29. The apparatus preferably further includes a needle valve 28 capable of resisting the vacuum and of adjusting the flow to between 1 and 12 liters per minute. As an optional feature, the generator can be started at the same time as the humidification period begins. This is then achieved with shut-off valve 26 and mixture bypass valve 29b. Shut-off valve 26 opens to let oxygen enter the generator. The ozone-oxygen mixture produced by the generator is then guided directly into the ozone converting unit 52 through mixture bypass valve 29b and vacuum pump 40. After a humidification period the oxygen-ozone mixture is guided into the sterilization chamber by opening the mixture supply valve 29a and closing the mixture bypass valve 29b. The oxygen-ozone mixture enters the chamber 10 until an ozone concentration of 85 milligrams per liter in the chamber is achieved. The time required for this step is dependent on the flow rate and concentration of the ozone gas in the mixture (preferably 10% to 12% by weight). At this point in time, the mixture supply valve 29a is closed to seal off the sterilization chamber and to maintain the humidified ozone/oxygen gas mixture in the chamber under vacuum.

Once the sterilization chamber is filled with the humidified sterilization gas (mixture of oxygen and ozone gas), the generator 22 is stopped, the oxygen shut-off valve 26 is closed, and the ozone is maintained in contact with the articles to be sterilized for about 15 minutes, for a sterilization chamber of a volume of 125 liters (4 cubic feet). At this stage, the sterilization chamber is still under the effect of a partial vacuum of about 670 mbar. In an optional second step, the pressure level is raised to about 900 mbar using oxygen as a filling gas. This pressure level is maintained for about 20 min. After the sterilization period, the vacuum is reapplied, preferably at a pressure of about 1.0 mbar again. Once the vacuum reaches 0.1 mbar, the humidification phase is recommenced, followed by the renewed injection of an oxygen/ozone sterilization gas mixture, followed by the sterilization period. The cycle of applying a vacuum of about 1.0 mbar, injecting sterilization gas, humidifying and sterilizing period, can be repeated, and the number of repeat sterilization cycles (mini cycles) selected to achieve complete sterilization of the instruments. Preferably, between any two successive sterilization cycles, a re-conditioning step is effected, as described above, to remove any condensed water from the sterilization chamber. The number of repeat cycles used in an experimental set-up including a 125 liters (4 cubic foot) chamber was 2 repeat cycles. This set-up conformed to the Security Assurance Level standards of the FDA (SAL 10-6).

To remove all remaining ozone and humidity in the sterilization chamber 10 after complete sterilization (after all successive sterilization cycles) a ventilation phase is engaged. The ventilation phase begins after the last sterilization cycle.

The chamber drainage valve 44 opens and the vacuum is applied down to approximately 13 mbar. Vapour intake valve 34 closes when the pressure reaches 60 mbar to evacuate the remaining ozone in the humidifier. Once the vacuum pressure of 13 mbar is obtained, drainage valve 44 closes and the intake valve 21 opens, admitting oxygen into the sterilization chamber 10. Once atmospheric pressure is reached, intake valve 21 is closed, the sterilization chamber drainage valve 44 opened, and vacuum reapplied until a pressure of 13 mbar is reached. The ventilation cycle is then repeated twice. Once the atmospheric pressure is reached after the last cycle, the door mechanism of the sterilization chamber is activated to permit access to the contents of the sterilization chamber. The ventilation phase has two functions. First, to remove all ozone residues in the sterilization chamber before opening the access door and, second, to ensure that the sterilized material is dry, which is achieved by evaporation when the vacuum pressure is applied.

The ozone-containing gas evacuated from the sterilization chamber 10 is passed over the ozone decomposing catalyst 52 of the ozone converting unit 50 prior to exhausting the gas to the atmosphere to ensure a complete decomposition of the ozone in the sterilization gas. The ozone generator 22 is used during only two portions of the sterilization cycle, the activation of the generator 22 (with optional valves 29a and 29b) and the evacuation of the sterilization chamber 10. During the start up phase of the generator 22, the mixture bypass valve 29b is opened and the ozone is guided across the catalyst. Once the start-up phase of the generator 22 is complete, the bypass valve 29b closes. During evacuation of the sterilization chamber 10, the sterilization chamber drainage valve 44 is opened and the ozone containing sterilization waste gas guided to the catalyst. Once the evacuation of the sterilization chamber 10 is completed, the drainage valve 44 is closed. The circulation of ozone is ensured by the vacuum pump 40, which operates during the whole sterilization cycle including all repeat cycles. If the ozone decomposing catalyst is located upstream of the vacuum pump this also ensures that the carulite is kept as dry as possible in order to avoid fouling of the catalytic material. Since the vacuum pump 40 is running during the whole sterilization process, the carulite is exposed to reduced pressures, even if it is not used for the decomposition of ozone. This forces evaporation of water contained in the catalyst, which may have been absorbed by the carulite during the evacuation of the sterilization chamber. If located downstream of the vacuum pump, the catalyst is preferably heated to keep the carulite sufficiently dry.

A system, such as the one described above, suitable for use with the method of the invention is capable of maintaining a relative humidity level of 90%, preferably 95%±5% or higher, throughout the sterilization cycle.

The energy needed to evaporate the water during the humidification phase is taken from many sources. It is taken from the structure of the humidifier unit and the sterilization chamber and from the material to be sterilized. This contributes to a further cooling of the chamber, and its contents. In effect, at 20° C., water boils up to an absolute pressure of 23.3 mbar and at 35° C., water boils up to an absolute pressure of 56.3 mbar. The vacuum in the sterilization chamber is preferably adjusted to a pressure where the boiling temperature of water is lowered below the temperature in the sterilization chamber. That boiling temperature may be so low that, depending on the energy available from the surrounding structure and gases, the water in the humidifier chamber will freeze before it gets vaporized. The humidifier may also be cooled by the evaporation process to a point where condensation freezes to the external surface of the humidifier. This can be avoided by heating the external surface of the humidifier sufficiently to keep the exterior of the humidifier unit and the water inside the humidifier chamber at room temperature, preferably at or above the temperature of the sterilization chamber. This is achieved with a heating arrangement (not illustrated) which will be readily apparent to the person of skill in the art.

The water vapour generated in the humidifier unit increases the relative humidity in the sterilization chamber. The humidification phase is continued until the relative humidity of the gas surrounding the medical instruments contained in the packaging pouches and containers reaches a minimum of 95%±5%, preferably 100%. For a sterilization chamber of an approximate volume of 125 liters, the water vapour admission increases the pressure to about 53 mbar in the sterilization chamber.

Oxygen/ozone-containing sterilization gas is injected into the humidified sterilization chamber at ambient temperature. For optimum operation of a sterilizer having a 125 liters chamber, a system is preferably used which is capable of generating an ozone flow in the range of about 1 to about 6 liters per minute, more preferably about 1.5 to 2 liters per minute, containing from about 160 to 200 mg/l of ozone to obtain at least a total of around 10,000 mg of ozone for each of the fillings of the sterilization chamber.

Changes and modifications in the specifically described embodiments can be carried out without departing from the scope of the invention which is intended to be limited only by the scope of the appended claims.

The invention claimed is:

1. A process for humidifying an atmosphere in a sterilization chamber to a target relative humidity, the process comprising the steps of
   a) providing an amount of water in a water reservoir at a reservoir temperature $T_s$ at or above a temperature of the chamber atmosphere $T_c$;
   b) reducing a pressure in the chamber to a value below the boiling point of water at the reservoir temperature $T_s$,
   c) bringing the reservoir into fluid communication with the chamber via a conduit for exposing the water in the reservoir at the temperature $T_s$ to the reduced pressure in the chamber for a preselected exposure time so that water in the reservoir is boiled and to allow resulting water vapour to enter the chamber and disconnecting said fluid communication after said preselected exposure time;
   and repeating at least steps b) and c) a plurality of times, wherein at least one of the amount, of water and the exposure time are controlled such that the relative humidity in the chamber progressively increases with each repetition until the target humidity is reached and wherein after each step c) the conduit is closed for a time sufficient to heat the water in the reservoir and to adjust the reservoir temperature $T_s$ so that the reservoir temperature $T_s$ is equal to or above the temperature $T_c$ of the chamber atmosphere, and a temperature differential $\Delta T$ during each step c) is controlled to maintain the temperature $T_c$ of the chamber atmosphere substantially constant, wherein $\Delta T$ is defined by the formula $\Delta T = T_s - T_c$.

2. A method according to claim 1, wherein the chamber and the reservoir are in fluid communication by a valve to open and close the conduit.

3. A method according to claim 1, wherein steps b) and c) are repeated from 5 to 27 times.

4. A method according to claim 1, wherein steps b) and c) are repeated at least 10 times and for each of the last 10 times the water vapour pressure in the chamber is increased by an amount in the range of from 0.01 to 5 Torr.

5. A method according to claim 1, wherein the temperature of the water in the reservoir is maintained from 0 to 3° C. above the temperature of the chamber.

6. A method according to claim 1, wherein the first time steps b) and c) are effected, the relative humidity in the chamber is increased to no more than 60% of the target relative humidity.

7. A method according to claim 1, wherein the number of times steps b) and c) are repeated and the increase in the relative humidity in the chamber after each step b) is selected to avoid substantially any condensation in the chamber.

8. A method of humidifying an enclosed space to a target relative humidity, the method comprising a plurality of humidification stages $S^x \ldots S^n$, wherein x is an integer from 1 to n and each x represents an individual stage, each said stage having a corresponding water vapour pressure $h_x, \ldots h_n$, and $h_n$ representing the water vapour pressure corresponding to the target relative humidity, each said stage $S_x$ including the steps of:
   a) supplying water vapour from a water vapour source to the enclosed space to increase the water vapour pressure in the enclosed space to at least the value $h_x$ corresponding to said stage $S_x$;
   b) disconnecting the source from the enclosed space for a preselected equilisation period; and
   c) repeating steps a) and b) until said water vapour pressure $h_n$ is reached in the space, wherein the water vapour source is a water reservoir, the temperature of the water vapour source is $T_s$, the temperature of the enclosed space is $T_c$, which is represented by the equation $T_s - T_c = \Delta T$ wherein $T_s$ is the same as, or higher than, $T_c$ so that $\Delta T_x \leq 0$, and step b) comprises disconnecting the source from the enclosed space for a time sufficient to adjust $T_s$ or $T_c$ to achieve the value for $\Delta T_x$ and controlling the temperature differential $\Delta T$ to maintain $T_c$ substantially constant.

9. A method according to claim 8, wherein n is from 5 to 27.

10. A method according to claim 8, wherein n is greater than 10 and for each stage $S_x$ of the last 10 stages, from n–10 to n, each increase in water vapour pressure from the previous stage $S_{x-1}$ to the stage $S_x$, said increase represented by $h_x - h_{x-1}$, is in the range of from 0.01 to 5 Torr.

11. A method according to claim 8, wherein the value of $h_1$ for the first stage represents a relative humidity of no more than 60% of the target value.

12. A method according to claim 8, wherein said space is a sterilization chamber for a humidified ozone sterilization process.

13. A method according to claim 8, wherein the number of stages and the corresponding water vapour pressure values are selected to avoid substantially any condensation in said space.

14. An apparatus for sterilization with humidified ozone, the apparatus comprising
   a sterilization chamber,
   a reservoir to hold water while in operation, to provide a source of water vapour to humidify the ozone,
   a conduit in fluid communication between the reservoir and the sterilization chamber,
   a valve in the conduit to open and close the conduit,
   a first heating means to control the temperature of the chamber,
   a second heating means to control the temperature of the reservoir,
   a first temperature sensing means to monitor the temperature of the sterilization chamber,
   a second temperature sensing means to monitor the temperature of the reservoir,
   a pressure sensing means to monitor the pressure in the chamber,
   vacuum means to reduce the pressure in the chamber,
   a processor to control the first and second heating means in response to information from the first and second temperature sensing means and the pressure sensing means,
   wherein the processor is programmed to effect a humidification of the sterilization chamber in a plurality of stages and to control a temperature difference between the first and second heating means to maintain the temperature of the chamber substantially constant.

15. An apparatus according to claim 14, wherein said plurality of stages is from 5 to 7.

16. An apparatus according to claim 14, wherein said plurality of stages is greater than 10 and, the processor is programmed to effect a water vapour pressure increase in each of the last 10 stages in the range of from 0.01 to 5 Torr.

17. An apparatus according to claim 14, wherein the processor is programmed to maintain the temperature of the reservoir form 0 to 3° C. above the temperature of the chamber.

* * * * *

UNITED STATES PATENT AND TRADEMARK OFFICE
CERTIFICATE OF CORRECTION

PATENT NO. : 7,608,217 B2 Page 1 of 1
APPLICATION NO. : 10/553740
DATED : October 27, 2009
INVENTOR(S) : Champagne It is certified that error appears in the above-identified patent and that said Letters Patent is hereby corrected as shown below:

On the title page item (86) should read
(86) PCT No.: PCT/CA2004/001636

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,608,217 B2
APPLICATION NO. : 10/553740
DATED : October 27, 2009
INVENTOR(S) : Champagne It is certified that error appears in the above-identified patent and that said Letters Patent is hereby corrected as shown below:

Claim 8 at column 19, line 34, the equation "$\Delta Tx \leq 0$" should read --$\Delta Tx \geq 0$--.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,608,217 B2  Page 1 of 1
APPLICATION NO. : 10/553740
DATED : October 27, 2009
INVENTOR(S) : Réal Champagne It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1008 days.

Signed and Sealed this

Twelfth Day of October, 2010

David J. Kappos
*Director of the United States Patent and Trademark Office*